United States Patent

Fu

(10) Patent No.: US 9,353,311 B2
(45) Date of Patent: May 31, 2016

(54) COMPOSITE VISIBLE COLORANT AND METHOD FOR QUANTITATIVE AMPLIFICATION

(71) Applicant: Bio-Rad Laboratories, Inc., Hercules, CA (US)

(72) Inventor: Rongdian Fu, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/510,036

(22) Filed: Oct. 8, 2014

(65) Prior Publication Data

US 2015/0104797 A1  Apr. 16, 2015

Related U.S. Application Data

(60) Provisional application No. 61/889,358, filed on Oct. 10, 2013.

(51) Int. Cl.
| | |
|---|---|
| *C12Q 1/68* | (2006.01) |
| *C09K 11/06* | (2006.01) |
| *G01N 21/64* | (2006.01) |
| *G01N 33/542* | (2006.01) |

(52) U.S. Cl.
CPC ............ *C09K 11/06* (2013.01); *C12Q 1/6804* (2013.01); *C12Q 1/6844* (2013.01); *G01N 21/6408* (2013.01); *G01N 21/6428* (2013.01); *C09K 2211/10* (2013.01); *C09K 2211/1018* (2013.01); *C12Q 2563/107* (2013.01); *G01N 33/542* (2013.01)

(58) Field of Classification Search
CPC . C12Q 1/6844; C12Q 2563/107; C09K 11/06
USPC ........................................ 435/6.1, 6.12, 91.1
See application file for complete search history.

(56) References Cited

U.S. PATENT DOCUMENTS

| | | |
|---|---|---|
| 5,736,333 A | 4/1998 | Livak et al. |
| 2006/0024743 A1 | 2/2006 | Mathies et al. |
| 2012/0164690 A1 | 6/2012 | Wang |
| 2012/0219957 A1 | 8/2012 | Kurkela et al. |
| 2014/0058043 A1 | 2/2014 | Miyamoto et al. |

FOREIGN PATENT DOCUMENTS

WO  2012/121225 A1  9/2012

OTHER PUBLICATIONS

International Search Report and Written Opinion from PCT/US2014/059710, dated Jan. 9, 2015.

*Primary Examiner* — Jezia Riley
(74) *Attorney, Agent, or Firm* — Kilpatrick Townsend & Stockton LLP (57) ABSTRACT

Methods and compositions for using colorants with real-time amplification reactions and normalization passive dyes are provided.

17 Claims, 3 Drawing Sheets

COMPOSITE VISIBLE COLORANT AND METHOD FOR QUANTITATIVE AMPLIFICATION

CROSS-REFERENCE TO RELATED PATENT APPLICATIONS

The present application claims benefit of priority to U.S. Provisional Patent Application No. 61/889,358, filed Oct. 10, 2013, which is incorporated by reference for all purposes.

BACKGROUND OF THE INVENTION

Real-time qPCR allows real time fluorescence detection and measurement of DNA amplification, and is often used for accurate quantitation of input DNA template in many molecular biology and biotech applications. There are several real-time qPCR chemistries and the most used two are: dsDNA binding (intercalating) fluorescence dyes, such as SYBR Green, and the 5'-nuclease hydrolysis fluorescence probe (TaqMan) method. The TaqMan method allows using multiple fluorescence report dyes, such as FAM, VIC, NED, 5- and/or 6-carboxy-X-rhodamine (e.g., available commercially as ROX™ and as SuperROX™ (from Biosearch Technologies, Petaluma, Calif.)), and CY5, each of which have different emission spectra for detection and measurement of multiple target DNA sequence amplifications in a single reaction.

There are many different real-time instrument platforms, such as 7500 and 7900 from Applied Biosystems, iQ5 and CFX96/384 from Bio-Rad, and some of them require an internal passive reference fluorescence dye for reporter dye fluorescence signal normalization from well to well to improve quantitation accuracy. Fluorescent dye ROX or a FRET ROX are often used as passive reference dyes (see, e.g., U.S. Pat. No. 5,736,333) in qPCR and RT-qPCR master mix products. Due to differences in design of thermal cyclers, some instruments employ a high concentration of 5- or 6-carboxy-X-rhodamine dye for normalization while others employ low concentration. The normal ROX dye has an excitation/emission maximum at 586/610 nm and can be excited efficiently on the 7500 and other "low ROX" instruments, which provide different excitation wavelength lights for each different fluorophore channels. The ROX dye cannot be excited efficiently on the 7900 "high ROX" instrument, which provides only a single 488 nm laser light for excitation of all different fluorophores, and hence a higher concentration of ROX is needed to generate required reference signal intensity for normalization. Typically, the ROX concentration used by a "high-ROX" platform is about 10-fold higher than that used by a "low-ROX" platform.

A FRET ROX is a FAM/ROX FRET-based oligo conjugation that can be excited both at 586 nm maximum as normal ROX dye, and at around 488 nm for the FAM fluorophore that upon being excited transfers the energy to the ROX fluorophore to emit fluorescence at 610 nm maximum. See, e.g., U.S. Pat. No. 5,736,333. A qPCR master mix with a single concentration of FRET ROX can be used on all different ROX-dependent instruments, whether it is a low ROX or high ROX instrument. A qPCR master mix with a defined concentration ratio of a normal ROX dye and a long Stokes-shift fluorescence dye that has an emission spectrum maximum similar to ROX but can be excited at around 488 nm can serve as a universal ROX reference dye similar to the FRET ROX, and can be used on different ROX-dependent qPCR instruments. See, e.g., US Patent Publication No. 2012/0164690.

PCR and other nucleic acid amplification reaction set-up on microwell-plate can involve pipetting a (1) reaction master mix that contains all assay components except the nucleic acid template, and (2) a DNA sample that contains the nucleic acid (e.g., DNA) template component separately into reaction wells. When this is done on a microwell plate with small volumes, it is easy to lose track of whether or not a component has been pipetted into a well, especially when a white or non-transparent well plate is used. Thus, reaction set-up errors can occur, resulting in failed PCR reactions. PCR master mixes with inert visible dye have been used to minimize pipetting errors for routine PCR and real-time PCR, and commercial products are available, such as RedTaq ReadyMix PCR Reaction Mix of Sigma Aldrich, Absolute Blue qPCR Mixes, DyNamo ColorFlash qPCR Kits, and Luminaris Color qPCR Master Mixes of ThermoScientific, and TaqMan GTXpress Master Mix (with tracking dye) of Life Technologies.

BRIEF SUMMARY OF THE INVENTION

It has been discovered that visible dye colorants can interfere with internal passive dye (e.g. ROX) signaling, resulting in instrument QC flag of "bad-passive-reference-signal", and poor Cq standard deviation (STDEV) and quantitation accuracy. This issue can be solved as described herein. Provided herein are composite visible dye formulations that solve this issue and that provide a universal visible colorant for using with any colorless qPCR master mixes on any real-time instrument platforms. In some embodiments, a standalone, concentrated composite colorant solution for use of pipetting tracking in reaction set-up with any commercial colorless PCR master mixes (with or without an internal passive reference 5- or 6-carboxy-X-rhodamine dye) without affecting its performance for required 5- or 6-carboxy-X-rhodamine dye normalization on its intended real-time PCR instrument, wherein, the composite colorant solution comprises at least 1.) a visible dye and 2.) a passive reference fluorescence dye that is able to compensate a reduction of an internal passive reference 5- or 6-carboxy-X-rhodamine dye signal caused by the visible dye absorption interference to the internal 5- or 6-carboxy-X-rhodamine dye dye excitation and/or emission during PCR, and wherein the passive reference dye is composed of either a FRET ROX or of a simple ROX and a long Stokes shift fluorescence dye, and is able to generate a good passive reference signal at around 610 nm wavelength on both a PCR instrument with an excitation light of around 488 nm wavelength and a PCR instrument with an excitation light of around 570 nm wavelength.

In some embodiments, an aqueous formulation (e.g., a composite colorant formulation) is provided, the formulation comprising: a visually-detectable dye; and an internal reference molecule comprising a first fluorophore, which first fluorophore upon excitation emits energy at a specific wavelength range; wherein the visually-detectable dye partially absorbs energy at the specific wavelength range; and the formulation does not comprise sufficient components for target nucleic acid amplification if added to a target nucleic acid and primers.

In some embodiments, the specific wavelength is between 615 and 625 nm.

In some embodiments, the first fluorophore is a 5- and/or 6-carboxy-X-rhodamine dye. In some embodiments, the concentration of the 5- and/or 6-carboxy-X-rhodamine dye is more than 100 nM. In some embodiments, the concentration of the 5- and/or 6-carboxy-X-rhodamine dye is more than 1000 nM.

In some embodiments, the internal reference molecule comprises a second fluorophore and a linker joining the first and second fluorophores such that excitation of the second fluorophore results in transfer of energy from the second fluorophore to the first fluorophore, which first fluorophore in turn emits energy at the specific wavelength range. In some embodiments, the second fluorophore is fluorescein amidite (FAM). For example, the internal reference molecule can be "FRET ROX".

In some embodiments, the visually-detectable dye (or dyes) is selected from the group consisting of Xylene Cyanol FF, Cresol Red, Tertrazine, Quinoline Yellow, m-Cresol Purple, Brilliant Blue, Patent Blue, Indigocarmine, Acid Red 1, Neutral Red, Bromocresol Green, Acid Violet 5, Bromo phenol blue, and Orange G.

In some embodiments, the visually-detectable dye is at an integer multiple of a visually-detectable concentration; and the internal reference molecule is at said integer multiple of a sufficient concentration to compensate for absorbance of a passive reference signal (e.g., in a qPCR reaction) by the visually-detectable dye at the specific wavelength range, wherein said integer multiple is between 2 and 1000.

In some embodiments, the formulation further comprises a long Stokes-shift dye different from the internal reference molecule, wherein the long Stokes-shift dye has a Stokes-shift that is greater than the Stokes-shift of the first fluorophore (which can be, for example, 5- and/or 6-carboxy-X-rhodamine dye), wherein the passive Stokes-shift dye has an emission wavelength maximum approximately the same as the first fluorophore emission wavelength maximum, and an excitation wavelength maximum significantly different than the first fluorophore excitation wavelength maximum. In some embodiments, the long Stokes-shift dye has a Stokes-shift of at least about 60 nm. In some embodiments, the long Stokes-shift dye has a excitation wavelength maximum of 550 nm or less. In some embodiments, said long Stokes-shift dye is a fluorescent dot.

In some embodiments, the internal reference molecule is a long Stokes-shift dye, wherein the passive long Stokes-shift dye has a Stokes-shifthaving an emission wavelength maximum approximately the same as a 5- and/or 6-carboxy-X-rhodamine dye emission wavelength maximum, and an excitation wavelength maximum significantly different than the 5- and/or 6-carboxy-X-rhodamine dye excitation wavelength maximum (e.g., an excitation wavelength maximum of about 550 nm or less).

In some embodiments, the formulation lacks a polymerase, nucleotides, or divalent cations.

Also provided is a method of forming a mixture capable of supporting nucleic acid amplification. In some embodiments, the method comprises combining the aqueous formulation as described above (or otherwise described as a "stock solution" herein) with at least a DNA polymerase, nucleotides, divalent cations, a passive reference dye for amplification normalization and a nucleic acid sample. In some embodiments, the method comprises combining the aqueous formulation with a real-time PCR master mixture comprising at least a DNA polymerase, nucleotides, divalent cations, a passive reference dye for amplification normalization, thereby forming a colored real-time PCR master mixture; and combining a nucleic acid sample with the colored real-time PCR master mixture.

Also provided is a method of performing a real-time quantitative polymerase chain reaction. In some embodiments, the method comprises performing a polymerase chain reaction (PCR) with a mixture comprising the aqueous formulation as described above (or otherwise described as a "stock solution" herein) and at least a DNA polymerase, nucleotides, divalent cations, a passive reference dye for amplification normalization, and a nucleic acid sample.

BRIEF DESCRIPTION OF THE DRAWINGS

FIG. 1 shows the principle of composite colorant for qPCR on all real-time PCR instruments. A.) Representatives of Real-time PCR instruments that require passive reference normalization for reporter signal analysis. B.) Passive reference "ROX" dyes used in qPCR master mixes: FRET ROX in all Applied Biosystems (AB)'s qPCR master mixes can be used at a single concentration on all AB's instruments; ROX can be used at a low concentration in a qPCR master mix for the "low ROX" instruments 7500 and ViiA7, but at a ~10× higher concentration in a master mix for the "high ROX" instrument 7900 due to its inefficient excitation with 488 nm light; long Stokes shift dye (LSD) can be used to generate "ROX" passive reference signal effectively on 7900, and when combined with a low concentration of ROX to form a "universal" composite ROX (uROX) in a master mix, the uROX can be used at a single concentration on all low and high ROX instruments. C.) A composite colorant comprising a visible blue dye and a "composite ROX" that includes a regular ROX and an LSD. The visible blue dye absorbs light at maximum 614 nm and interferes and reduces ROX signal when added into a colorless qPCR master mix. The composite ROX compensates the loss of ROX signal by the visible blue dye to maintain a good passive reference signal for reporter signal normalization.

DETAILED DESCRIPTION OF THE INVENTION

I. Introduction

Stock solutions comprising at least one visually detectable inert dye (also referred to herein as a "visible dye" or "colorant") and at least one passive reference dye, e.g., 5- and/or 6-carboxy-X-rhodamine, and methods for using such stock solutions with colorless real-time PCR master mixes, are provided. It has been discovered that visible dyes (e.g., for use in confirming deposit of reagents into microplates) can be combined with passive reference dyes as stock solutions that, when added to qPCR reactions, can adjust the concentration of the total passive reference dye(s) to compensate for any interference of emission or excitation of the internal passive reference dye(s) (e.g., in the master mix) caused by the visible dye alone. Prior to this discovery, one often could not successfully add a visible dye colorant to an amplification master mix that comprises a passive reference dye (e.g., ROX) without degrading the normalization function of the internal passive reference dye because the colorant would interfere with the passive reference dye signal, thereby degrading or ruining normalization using the passive reference dye. In view of the discovery, a composite colorant stock solution is provided comprising a visible dye and an amount of the passive reference dye to compensate for the interference caused by the visible dye. This stock solution will typically not be able to support amplification itself, but instead can be added to off-the-shelf or otherwise pre-made real-time qPCR master mixes that themselves can support amplification. Thus the combination of the stock solution and the master mix allows for generating a colored master mix that, while being colored for ease of tracking, will support amplification and allow for normal passive reference normalization in spite of the presence of a visible dye.

As explained in more detail below, in one aspect, the visible dye is combined with a passive reference dye that has an excitation/emission spectra the same as or similar to the passive reference dye(s) (referred to as an "internal passive reference dye" when in the master mix—as opposed to in the composite stock solution as discussed below) in the master mix. The amount of the passive reference dye(s) is(are) sufficient to compensate for the reduction of internal passive reference dye(s) signal (at the emission wavelength) caused by the visible dye alone, such that when the visible dye/passive reference dye(s) stock solution is combined with a real-time amplification master mix comprising the internal passive reference dye(s), the total passive reference dye concentration will be sufficient to generate a normal passive reference signal for good normalization performance for the qPCR data analysis.

II. Formulations

Provided herein are composite colorant (i.e., comprising at least one visually-detectable dye(s) and one or more passive reference dyes) formulations. The formulations will generally be concentrated stock solutions for ease of use, meaning that the concentration of the components are at a set integer multiple of their ultimate desired (e.g., as discussed above) concentration, such that a small amount of the stock solution can be added to a larger volume of a real-time PCR mastermix or other component solutions (e.g. assay primers/probes mixture or DNA samples) to be visually tracked for pipetting accuracy. For example, the formulation concentration (i.e., all components of the formulation) can be set at a concentration of "10×", "20×," "50×," "100×," "200×," 500×," or more. This allows for a relatively small amount of stock composite colorant solution to be added to amplification reaction components to generate a colored mixture, for example, that can subsequently be added to a plurality of receptacles (e.g., a microwell plate) comprising, or soon to comprise, sample nucleic acids and/or other reaction components. The small amount of stock composite colorant solution added to an amplification reaction mixture can in some embodiments be less than 10%, 5%, 2%, or 1% of the volume of the amplification reaction, thereby causing only an insignificant change in overall concentration of reaction mixture components while adding composite colorant solution. As an example, one microliter of a 200× stock composite colorant solution can be added to a 100 µl 2× amplification master mix thereby achieving a "2×" concentration of visually-detectable dye and of additional compensating passive reference dye(s) while altering concentrations of the 2× amplification master mix components by less than 1%, i.e., insignificantly.

In some embodiments, the composite colorant stock solution is an aqueous solution, optionally comprising a buffer, and otherwise consisting of the visible dye and the passive reference dye(s).

In addition to the ingredients above, in some embodiments, the stock solutions can further comprise or consist of, for example, a buffer (e.g., Tris buffer, or Tris-EDTA buffer), a detergent (e.g., a non-ionic detergent such as Triton X-100—to prevent the dye from sticking to plastic surface through hydrophobic interaction), and/or a fungicide or other preservative.

Visible Dyes

Visually-detectable dyes (sometimes referred to herein as colorants) that can be used as described herein include any dye that can be seen with the naked eye at the concentration used and that does not significantly interfere with nucleic acid amplification. In some embodiments, the visually-detectable dye can be selected from Xylene Cyanol FF, Cresol Red, Tertrazine, Quinoline Yellow, and m-Cresol Purple. Other candidate visible dyes that can be used include, but are not limited to, Brilliant Blue, Patent Blue, Indigocarmine, Acid Red 1, Neutral Red, Bromocresol Green, Acid Violet 5, Bromo phenol blue, and Orange G, e.g., as listed in U.S Patent Publication No. 2012/0219957. Other exemplary visually-detectable dyes include those listed in U.S. Pat. No. 6,942,964. The concentration of the visually-detectable dye will be a sufficient concentration for visualizing the dye in a colored reaction component solution, or when in a stock solution, an integer multiple (e.g., 100×, 500×, 1000×) of that sufficient concentration.

Passive Reference Dyes

Passive reference dyes are dyes that provide an internal reference to which the reporter dye signal can be normalized during data analysis. The dyes are "passive" as known in the art, i.e., in that the signal of the dyes do not significantly vary in the presence of various quantities of double-stranded nucleic acids. At least one passive reference dye is included in the composite colorant formulation. In addition, a passive reference dye will also generally be included in a real-time PCR master mix for normalization. Generally, though not always, the same passive reference dye is used in the composite colorant formulation and the master mix. Strictly for convenience of discussion, when the passive reference dye is in the master mix is discussed, the term "internal passive reference dye" will be used. As an example, ROX in a composite colorant stock solution is referred to as a "passive reference dye", while ROX in a qPCR master mix is referred to as a "internal passive reference dye." Thus, "passive reference dye" and the "internal passive reference dye" used in the qPCR master mix will generally be the same, and generally will be 5- and/or 6-carboxy-X-rhodamine. The passive reference dye(s) will generally be a fluorescence dye(s) with a same or similar excitation/emission spectra as the internal passive reference dye(s) used in the real-time amplification master mix with which the stock solution of this invention will be used for reaction set-up pipetting tracking. For example, if the master mix uses 5- and/or 6-carboxy-X-rhodamine (e.g., ROX) as the passive reference dye for normalization, then the passive reference molecule in the composite colorant stock formulation will also be 5- and/or 6-carboxy-X-rhodamine, or a combination of a ROX dye and a long Stokes shift dye that collectively gives a excitation/emission spectra similar to the FRET ROX for passive reference purpose. If the master mix uses FRET-ROX (i.e., FAM linked to ROX, e.g., as described in U.S. Pat. No. 5,736,333) then the passive reference molecule in the stock formulation will also be FRET-ROX, or a combination of a ROX dye and a long Stokes shift dye that collectively gives a excitation/emission spectra similar to the FRET ROX for passive reference purpose. The concentration of the passive reference dye in the composite colorant will be a concentration to approximately compensate for interference the visually-detectable dye causes for signal from the internal reference dye. For example, if introduction of the visually-detectable dye into the master mix results in a 10% decrease in signal from the internal passive reference dye in the PCR reaction, then the composite colorant stock formulation will contribute an additional 10% of the passive reference signal (such that when the stock formulation and master mix are combined, the resulting reaction mixture has a similar passive reference dye signal as without using the composite colorant). As discussed above, as the visually-detectable dye/passive reference molecule formulation is typically to be used as a stock solution, the concentration of the passive reference dye in the stock solution will be the integer multiple of the compensatory amount of internal passive reference molecule.

Long Stokes-Shift Dyes

In some embodiments, the stock formulations will further comprise a "long Stokes-shift dye," for example as described in US Patent Publication No. 2012/0164690.

Thus, in one aspect, the visible dye is combined with (1) and (2) below to form the composite colorant:

(1) A first passive reference dye with an excitation/emission spectra same as or similar to the internal reference dye (e.g., 5- and/or 6-carboxy-X-rhodamine) with an amount of the reference dye as described above, i.e., formulated so as to provide a sufficient amount of passive dye reference signal to compensate for the reduction of internal reference dye signal. For example, the stock formulation can comprise a sufficient amount of 5- and/ or 6-carboxy-X-rhodamine to compensate for the reduction of 5- and/or 6-carboxy-X-rhodamine signal caused by the visible dye alone on a "low ROX" instrument (e.g. 7500 series Real-Time PCR Instrument and ViiA 7 Real-Time PCR Instrument from Applied Biosystems).

(2) A second passive reference dye (referred to here as a "long Stokes shift dye"). The long Stokes shift reference dye has a Stokes shift that is greater than the Stokes-shift of the internal reference dye (e.g., 5- and/or 6-carboxy-X-rhodamine) and has an emission wavelength maximum approximately the same as the internal reference dye emission wavelength maximum, and an excitation wavelength maximum significantly different than the internal reference dye excitation wavelength maximum. The concentration of the long Stokes shift dye is formulated so as to compensate for the reduction of the passive reference signal caused by the visible dye alone on a "high ROX" instrument (e.g. 7900 series Real-time PCR Instrument from Applied Biosystems).

The Stokes-shift refers to the difference between the excitation and emission wavelength of the dye.

The long Stokes-shift dye is "long" because the dye is excited at a wavelength significantly different than that of 5- or 6-carboxy-X-rhodamine dye (which has an excitation maximum at ~575 nm), but has an emission wavelength maximum substantially the same as 5- or 6-carboxy-X-rhodamine dye (which has an emission wavelength maximum of ~620 nm), and thus has a longer Stokes shift than the 5- or 6-carboxy-X-rhodamine dye. The inclusion of the long Stokes-shift dye allows the dye mixture to be used at a single concentration on both high and low concentration ROX instruments. The concentration of the long Stokes-shift dye in an amplification reaction is determined such that the combined signal of the long Stokes-shift dye and the first passive reference dye (which can be, but is not limited to, 5- or 6-carboxy-X-rhodamine dye) is sufficient for use in a high concentration passive reference dye real-time PCR instrument to normalize data. When used on a low concentration passive reference dye real-time PCR instrument, the fluorescent dye with a long Stokes-shift will not be excited in the passive reference dye (e.g., 5- or 6-carboxy-X-rhodamine) channel, thus not generating any additional signal in the channel to be detected/used for passive reference dye normalization. The signal generated by the low concentration of first passive reference dye present in the mixture is used for normalization instead. As a result, this pre-mix with a single concentration of composite colorant can be used on both "high-passive reference dye" and "low-passive reference dye" instruments, as well as on instruments requiring no passive reference normalization, and thus allows the mixture to be "universally" applicable regardless of the instrument used.

As discussed above for the other dyes, when formulated into a stock solution, the long Stokes-shift dye concentration is an integer multiple (e.g., 2-1000×) of the working concentration described above.

Any long Stokes-shift dye can be used according to the invention so long as the dye has an excitation wavelength maximum that significantly differs from that of the first passive reference dye (e.g., 5- or 6-carboxy-X-rhodamine dye) and has an emission wavelength maximum that can be detected in combination with the first passive reference dye with the same detection channel. Accordingly, the excitation (or absorbance) peak wavelength maximum should peak at less than about 560 nm where 5- or 6-carboxy-X-rhodamine dye is the passive reference dye. In some embodiments, the emission peak wavelength maximum of the long Stokes-shift dye will typically be between 590-630, 590-610, or 610-630, e.g., 615-625, e.g., about 620 nm. The dyes will generally not have significant affinity for nucleic acids. The dyes, for example, can be fully or partially soluble in aqueous solutions or can be insoluble solids that evenly distribute in aqueous solution (e.g. fluorescent particles).

The long Stokes-shift dye can also be selected such that the excitation wavelength maximum of the long Stokes-shift dye and the first passive reference dye are sufficiently different that, if desired, the passive reference dye can be excited without substantially exciting the long Stokes-shift dye. Thus in some embodiments, the long Stokes-shift dye has an excitation wavelength maximum of less than 460, 470, 480, 490, 500, 510, 520, 525, 530, 540, 550, 560 nm, e.g., 470-510, 490-510, 480-500 nm, etc. The particular excitation wavelength maximum can be any wavelength so long as it does not significantly overlap with the excitation wavelength maximum of the passive reference dye, and is compatible with real-time amplification instruments optical design. In some embodiments, the Stokes shift (the difference between the excitation and emission wavelength maximum) of the dye is at least, e.g., 60, 75, 100, 150 nm or more (i.e., at least 5, 10, 25, 50 nm, or more from the passive reference dye excitation wavelength maximum). In some aspects, the Stokes shift of the dye is about 80 nM and in some cases an excitation maximum around or at 532 nm. An example of such a dye is the mFluor™ Green 620 SE dye (available commercially from, e.g., AAT Bioquest (Sunnyvale, Calif.).

Another exemplary long Stokes-shift dye is Chromeo™ 494, which is commercially available from, for example, Active Motif (Carlsbad, Calif.). Chromeo 494 has the following chemical content: $C_{26}H_{32}N_2O_4$, MW 436.55. Chromeo 494 can be excited at 488 nm but emits at about 620 nm (as FRET ROX will do on a "high ROX" instrument such as the 7900HT Real-Time PCR Instrument (Applied Biosystems)).

Another exemplary long Stokes-shift dye has the following formula:

This dye is available commercially as DY-510XL (Dyomics, Jena, Germany). Various modifications of the above-dye are available (e.g., from Dyomics), including, e.g., carboxylic acid ($C_{29}H_{34}N_2O_7S$; MW 554.67), NHS-ester ($C_{33}H_{37}N_3O_9S$; MW 651.74), amino-derivative ($C_{31}H_{41}N_4O_6SCl$; MW 633,21), maleimide ($C_{35}H_{40}N_4O_8S$; MW 676.80), and dUTP ($C_{41}H_{48}N_5O_{20}P3S*4Li$; MW 1083.61) modifications. It is believed such modified dyes as well as other modified versions can be used according to the present invention. For example, the carboxylic acid modified version of the above dye has an adsorption/emission maxima at 509 nm/590 nm.

In some embodiments, the colorant mixture will comprise the long Stokes-shift dye in a form free from chemical modification or conjugation. Alternatively, the long Stokes-shift dye can comprise (e.g., can be conjugated to) one or more further chemical moieties so long as they do not significantly affect the excitation or especially the emission wavelength maximum of the dye. Thus, in some embodiments, the long Stokes-shift dye comprises a linker or other moiety. Exemplary moieties include but are not limited to, e.g., an azide, alkyne, carboxylic acid, a NHS-ester, biotin or streptavidin. It will be appreciated that other moieties can also be linked to a dye without significantly affecting the dye's activity as described above. In some embodiments, the long Stokes shift dye is linked to a peptide, oligonucleotide, or other molecule.

In some embodiments, the long Stokes-shift dye is linked to, or is otherwise incorporated with, or contained in a solid support. Exemplary solid supports include but are not limited to beads, particles, and microspheres.

In some embodiments, the long Stokes-shift dye comprises or is a fluorescent dot. Exemplary fluorescent dots include, but are not limited to, quantum dots (see, e.g., U.S. Pat. Nos. 5,482,890, 5,229,320, and 6,326,144) and semiconducting polymer dots (Pdots), including but not limited to amphiphilic polystyrene semi-conducting polymer (see, e.g., Wu et al., *J Am Chem Soc* 132(43):15410-7 (2010)).

In addition to dyes, other fluorescent agents having a long Stokes shift (i.e., having an excitation wavelength maximum that significantly differs from that of the passive reference dye (e.g., 5- or 6-carboxy-X-rhodamine dye) and having an emission wavelength maximum that can be detected in combination with the passive reference dye with the same detection channel) can also be used as described herein. Other possible agents include, but are not limited to, fluorescent proteins.

The concentration of the particular long Stokes-shift dye or agent used will vary depending on the various parameters, including the quantum yield of the particular dye used. Useful concentrations for the invention can be determined empirically, and can depend, for example, on the precise visible dye used and the signal strength in the FRET or ROX channel.

Amplification Master Mixes

Figure 1:
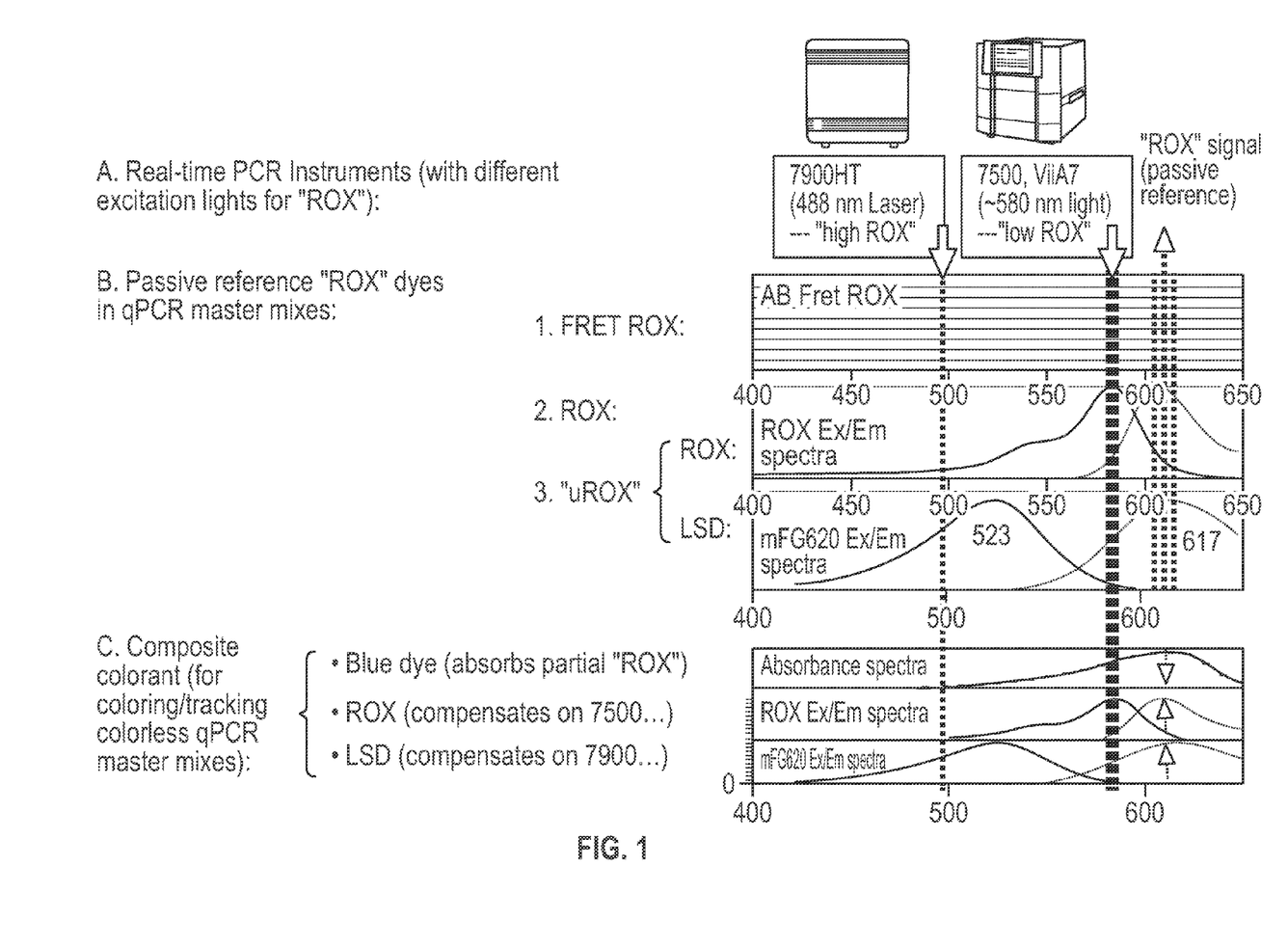

When ready for use, the composite colorant stock solution can be mixed with one or more solution used for reaction set-up for real-time amplification. Thus, in some embodiments, the colorant/dye stock solution is combined with a colorless real-time amplification (e.g., qPCR) master mix comprising a passive reference dye (e.g., 5- or 6-carboxy-X-rhodamine, or FRET ROX). A "master mix" refers to a mixture of components sufficient for amplification with the exception of assay primers/probes and template DNA, and will typically include, e.g., a polymerase, free nucleotides (e.g., dNTPs), $Mg^{++}$, a pH buffer and optionally additives for improving PCR performance and reagent stability. Other components can also be included. Master mixes can also contain an internal passive reference dye, e.g., 5- or 6-carboxy-X-rhodamine (e.g., "ROX") dye (see FIG. 1) for use on different real-time PCR instruments that require a passive reference for reporter signal normalization in qPCR data analysis to improve quantification accuracy. One benefit of the visible dye/passive reference dye composite colorant stock solutions described herein is that they can be added to off-the-shelf real-time amplification master mixes designed to be used on any real-time PCR instruments, whether it requires no-ROX (e.g. CFX96/384 from Bio-Rad), low-ROX (e.g. 7500 and ViiA 7 Real-Time PCR Instruments from Applied Biosystems), or high-ROX (e.g. 7900 Real-time PCR instrument from Applied Biosystems) reference dye concentrations.

The master mixes can further contain one or more reagents useful and/or required for amplification or detection of the sample. Exemplary possible reagents include, but are not limited to, one or more salt, one or more buffer, one or more nucleic acid polymerase and/or reverse transcriptase, one or more an oligonucleotide primer, as well as other reagents that improve the amplification.

In some embodiments, the master mixture does not include an oligonucleotide primer, thereby allowing a user to add a primer(s) as desired. In other embodiments, the master mixture can include one or more oligonucleotide primer. Oligonucleotide primers can be any oligonucleotide of two or more nucleotides in length. In some embodiments, PCR primers are about 15 to about 30 bases in length, and are not palindromic (self-complementary) or complementary to other primers that can be used in the reaction mixture. Primers can be, but are not limited to, homopolymers, primers specific to a target RNA template (e.g., a sequence specific primer), or mixtures of random primers. Any primer can be synthesized by a practitioner of ordinary skill in the art or can be purchased from any of a number of commercial venders (e.g., from Boehringer Mannheim Corp., Indianapolis, Ind.; New England Biolabs, Inc., Beverley, Mass.; Pharmacia LKB Biotechnology, Inc., Piscataway, N.J.; Integrated DNA Technology, Coralville, Iowa; Eurogentec, San Diego, Calif.; Sigma Genesys, The Woodlands, Tex.). Optionally, the mixtures can comprise one or more labeled oligonucleotide. Labels can include, for example, fluorescent labels including but not limited to FRET labels. Such labeled oligonucleotides can be useful, for example, for TAQMAN™ amplification as detailed further below.

Nucleotide bases in the master mix can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin).

In some embodiments, the nucleotides are deoxynucleoside triphosphates, dNTPs (e.g., dATP, dCTP, dGTP, dTTP, dUTP, α-thio-dNITs, biotin-dUTP, fluorescein-dUTP, digoxigenin-dUTP, 7-deaza-dGTP). dNTPs are also well known in the art and are commercially available venders (e.g., from Boehringer Mannheim Corp., Indianapolis, Ind.; New England Biolabs, Inc., Beverley, Mass.; Pharmacia LKB Biotechnology, Inc., Piscataway, N.J.). In some embodiments, the nucleotides comprise 1, 2, 3, or 4 different deoxynucleoside triphosphates selected from dATP, dCTP, dGTP, dTTP, and dUTP.

The nucleotides can be present in the master mix in any useful concentration. In some embodiments, the nucleotides are present in an amount from about 1 nM to about 1000 nM. In other embodiments, the nucleotide are present in an amount from about 10 nM to about 750 nM. In still other embodiments, the nucleotides are present in an amount from about 100 nM to about 500 nM. One of skill in the art will appreciate that other concentrations of nucleotides can also be useful.

Buffering agents and salts in the master mix provide appropriate stable pH and ionic conditions for nucleic acid synthesis, e.g., for DNA polymerase activity. A wide variety of buffers and salt solutions and modified buffers are known in the art that can be useful in the present invention, including agents not specifically disclosed herein. Exemplary buffering agents include, but are not limited to, TRIS, TRICINE, BIS-TRICINE, HEPES, MOPS, TES, TAPS, PIPES, and CAPS. Exemplary salt solutions include, but are not limited to solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents can be present in any concentration. In some embodiments, the buffer is present in an amount from about 0.1 mM to about 1000 mM. In other embodiments, the buffer is present in an amount from about 1 mM to about 500 mM. In still other embodiments, the buffer is present in an amount from about 5 mM to about 250 mM. One of skill in the art will appreciate that other concentrations of buffer are useful.

The salts of the present invention can be present in any concentration. In some embodiments, the salt is present in an amount from about 0.01 mM to about 1000 mM. In other embodiments, the salt is present in an amount from about 0.1 mM to about 500 mM. In still other embodiments, the salt is present in an amount from about 1 mM to about 100 mM. One of skill in the art will appreciate that other concentrations of salts are useful.

One or more of these additives can be incorporated in the master mix to optimize the generation and replication of nucleic acids from a ribonucleic acid template. Additives can be organic or inorganic compounds Inhibition-relieving agents useful in the present invention include, but are not limited to, polypeptides such as; human serum albumin, bovine serum albumin (BSA), ovalbumin, albumax, casein, gelatin, collagen, globulin, lysozyme, transferrin, myoglobin, hemoglobin, α-lactalbumin, fumarase, glyceraldehyde-3-phosphate dehydrogenase (GAPDH), amyloglucosidase, carbonic anhydrase, β-lactoglobulin, aprotinin, soybean trypsin inhibitor, trypsinogen, phosphorylase b, myosin, actin, β-galactosidase, catalase, tryptic soy digests, tryptose, lectins, *E. coli* single-stranded binding (SSB) protein, phage T4 gene 32 protein, and the like, or fragments or derivatives thereof. Examples of nonpolypeptide additives include, but are not limited to; tRNA, rRNA, sulfur-containing compounds, acetate-containing compounds, dimethylsulfoxide (DMSO), glycerol, formamide, betain, tetramethylammonium chloride (TMAC), polyethylene glycol (PEG), TWEEN 20 non-ionic surfactant, NP 40, non-ionic surfactant, ectoine, and polyols. Exemplary additives include DMSO, glycerol, formamide, betain, TMAC, PEG, TWEEN 20 non-ionic surfactant, NP 40 non-ionic surfactant, ectoine, polyols, *E. coli* (SSB) protein, Phage T4 gene 32 protein, and BSA.

In addition, the master mixes can include agents which provide for detection of the amplification products. For example, the pre-mixes can include appropriate hybridization probes for homogenous real time detection of amplification products. In some embodiments, these probes can be appropriately labeled with fluorescent moieties. Other possible components include additional dyes that bind to double-stranded DNA. In some embodiments, the dye can be SYBR green.

DNA polymerases useful in the master mixes can be any polymerase capable of replicating a DNA molecule. Exemplary DNA polymerases are thermostable polymerases, which are especially useful in PCR, e.g., thermophilic polymerases. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothermophilus* (Bst), *Sulfolobus acidocaldarius* (Sac), *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the DNA polymerase can be Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENTT™, and active mutants, variants and derivatives thereof. It is to be understood that a variety of DNA polymerases can be used, including DNA polymerases not specifically disclosed above, without departing from the scope or preferred embodiments thereof.

In some embodiments, the polymerase included in the master mix is a hybrid polymerase comprising a polymerase domain and a DNA binding domain. Such hybrid polymerases are known to show an increased processivity. See e.g., U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases.

In one aspect, the hybrid polymerase lacks 3'-5' exonuclease activity. In one embodiment, such hybrid polymerases comprise a double point mutation in the polymerase domain that provides this exonuclease deficiency. A variety of mutations can be introduced into a native polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17 (1991) and Derbyshire et al., *Methods in Enzymology* 262:363 85 (1995). It will be understood that while the above-described mutations were originally identified in one polymerase, one can generally introduce such mutations into other polymerases to reduce or eliminate exonuclease activity. In a specific embodiment, a polymerases of the invention comprise the double point mutation D141A/E143A in the polymerase domain. The phrase "corresponding to a position," in reference to polymerase amino acids, refers to an amino acid that aligns with the same amino acid (e.g., D141 or E143) in a reference polymerase amino acid sequence (e.g., SEQ ID NO:2). Sequence comparisons can be performed using any BLAST including BLAST 2.2 algorithm with default parameters, described in Altschul et al., *Nuc. Acids Res.* 25:3389 3402 (1977) and Altschul et al., *J. Mol. Biol.* 215:403 410 (1990), respectively.

In some embodiments, the DNA binding domain of hybrid polymerases are from a thermostable organism and provides enhanced activity at higher temperatures, e.g., temperatures above 45° C. For example, Sso7d and Sac7d are small (about 7 kD MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the $T_m$ of DNA by up to 40° C. under some conditions (McAfee et al., Biochemistry 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence. In further embodiments, hybrid polymerases of use are described for example in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. Examples of hybrid polymerase proteins and methods of generating hybrid proteins are also disclosed in WO2004011605. Methods for producing polymerases comprising a polymerase domain and a nucleic acid binding domain are described, for example, in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898.

In some embodiments, the polymerases of the master mix are prepared for use in "hot start" methods to decrease the generation of primer dimers and unspecific amplification products at ambient temperatures. A number of hot-start methods are known. These include physical separation of the polymerase, use of nucleic acid additives (i.e. aptamers) to inhibit extension reactions at low temperatures, and modifications to the active site of the polymerase. Often, it may be desirable to use "hot start" polymerases. In a hot-start polymerase, a molecule is typically bound to the enzyme at the active site to inhibit polymerase activity at lower temperatures. The molecule is removed at high temperatures (e.g., at 95° C.) to allow the polymerase to function at the desired point of the process. The molecule can be one or more antibody, peptide, or a small organic molecule. For example, hot-start can be achieved using one or more antibody that binds to a polymerase with high affinity at ambient temperatures in an inhibitory manner. The complex is dissociated in a high temperature preheating step.

A polymerase may also be chemically modified for hot-start. Heat labile blocking groups are introduced into the polymerase, which render the enzyme inactive at room temperature. These blocking groups are removed at high temperature prior to cycling such that the enzyme is activated. Heat labile modifications include coupling citraconic anhydride or aconitric anhydride to lysine residues of the enzyme are known in the art, see e.g., U.S. Pat. No. 5,677,152.

U.S. Patent Application Publication No. 2003/0119150 also discloses a concept of hot start PCR that employs a thermostable exonuclease and a polymerase. This method is based on preventing primer elongation at low temperatures by introducing chemical modifications at the 3' end of at least one primer. A thermostable exonuclease is used that is inactive at ambient temperatures or below. Upon temperature increase, the exonuclease becomes active and capable of removing the 3' modification of the primer to enable it to participate in the amplification reaction. U.S. 20030119150, which is hereby incorporated by reference in its entirety for all purposes and in particular for all teachings related to hot-start methods, further teaches that when hybridization probes are used for real-time monitoring, e.g., TaqMan hybridization probes, Molecular Beacon oligonucleotides, or two oligonucleotide hybridization methods, the presence of a thermostable exonuclease III requires a suitable blocking method for the 3' end of the detection probe to avoid 3' digestion.

In certain aspects, the master mix can include an additional compound as an additive to improve efficiency in amplification reactions. Exemplary additives are described in, e.g., PCT WO2010/080910. In some embodiments, the additive is an osmolyte included in an amplification reaction of the invention to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds that are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine.

III. Methods

Methods of making and using the composite colorant stock solution comprising a visually-detectable dye and an internal passive reference dye are provided. The stock solution can be mixed with various components to form a visually-detectable amplification reaction. The colored stock solution can be added to, for example, a real-time qPCR master mix, the solution(s) of sample(s), a mixture of a master mix and assay primers/probes, or a mixture of a master mix and a sample solutions. In some embodiments, a concentrated stock solution of the composite colorant is added to a qPCR master mix solution comprising a passive internal dye and, for example, having sufficient components to support amplification of a target nucleic acid in the presence of the target nucleic acid and primers. Generally, the stock solution will be concentrated as a multiple integer of the ultimate desired concentration (e.g., 20×, 100×, 500×, 1000×) such that a relatively small amount of the colorant/internal reference molecule mixture. In any case, the method of forming the mixture can involve adding each component (e.g., polymerase nucleotides, buffer, etc.) separately, or as a master mix, as described above. In some embodiments, the methods of forming an amplification reaction will include adding a nucleic acid sample and/or primers. In some embodiments, a plurality of receptacles will receive the mixture, wherein the visually-detectable dye allows the user to track which receptacles have received the master mix/visually-detectable dye mixture.

Methods of performing an amplification reaction using the master mix/colorant mixture are also provided. Once the master mix/colorant mixture comprises a nucleic acid, an amplification reaction can be performed. Methods of performing real-time amplification (i.e., DNA amplification) are known. Quantitative PCR methods involve amplification of an nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. Methods of quantitative amplification are disclosed in, e.g., U.S. Pat. Nos. 6,180,349; 6,033,854; and 5,972,602. Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases logarithmically, the signal intensity increases to a measurable level and then enters into a non-logarithmic phase, and then finally reaches a plateau in later cycles. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., PNAS USA 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™)

In other embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than, for example, primer-dimers, etc.

Normalization using the passive reference dye involves the further step of monitoring fluorescence of the passive reference dye during each amplification cycle. Because the passive reference dye does not interact with nucleic acids or is otherwise affected by the amplification reaction, the signal from the internal reference dye provides a normalizing factor, e.g., so as to normalize the reaction for such factors that vary from reaction to reaction, e.g., volume or reagent quantities. Thus by examining the ratio of the fluorescent intensities of a probe and the internal reference molecule, the effects of most sources of systematic variability are eliminated. As described above, different real-time PCR instruments may use different light sources for fluorescence dye excitation. The "Low ROX" concentration instruments excite the ROX dye at or near its excitation maximum of about 580 nm. Exemplary low ROX concentration instruments include, e.g., 7500 and ViiA 7 real-time PCR instruments from Applied Biosystems. Other instruments excite ROX at a wave length around 488 nm, substantially different from its excitation maximum. In these instruments, significantly more (e.g., ten times more) ROX dye is required because the excitation of the passive reference dye is not at the maximum but instead is at a less optimal (for exciting the passive reference dye) wavelength. Exemplary high concentration instruments include, e.g., 7900HT and StepOne Plus Real-time PCR instruments from Applied Biosystems.

EXAMPLE

Example 1

Visible Dye Interference and its Prevention with a Composite Colorant

Real-time PCR reactions were prepared as follows:

No colorant control: Real-time PCR reactions were prepared with Bio-Rad SsoAdvanced Universal SYBR Supermix (2×). The final reaction mix contains 1× the Supermix, 500 nM each of forward and reverse primers for a 226 bp human GAPDH gene amplicon assay, and 5 ng of human genomic DNA per reaction. Concentrations of ROX and a long Stokes-shift dye provided from the 2× Supermix allow for appropriate ROX normalization when running the qPCR reaction on both high ROX and low ROX instruments. There was no visible dye colorant added to the reaction.

Reactions with visible dye colorant: Real-time PCR reactions were prepared with Bio-Rad SsoAdvanced Universal SYBR Supermix (2×) as the no colorant control above, but with an addition of the visible dye Xylene Cyanol FF at a final concentration of 1× (0.00325 mg/ml) to demonstrate the visible dye interference to the ROX normalization.

Reactions with a composite colorant mixture of a visible dye and a long Stokes-shift dye: Real-time PCR reactions were prepared with Bio-Rad SsoAdvanced Universal SYBR Supermix (2×) as the no colorant control above, but with an addition of a composite colorant mixture of the visible dye Xylene Cyanol FF at a final concentration of 1× (0.00325 mg/ml) and the long Stokes-shift dye mFG620C at a final concentration of 1× (0.1 ng/ml) to demonstrate the compensating effect of the long Stokes-shift dye to the visible dye to avoid the visible dye interference to the ROX normalization. All the above qPCR reactions were run in 20 μl/reaction on an AB7900 real-time PCR instrument, with a thermal cycling protocol of an initial denaturation at 98 C for 3 min followed by 40 cycles of denaturation at 98 C for 10 sec and annealing/extension at 60 C for 30 sec. Data analysis was done with ROX normalization applied.

Figure 2:
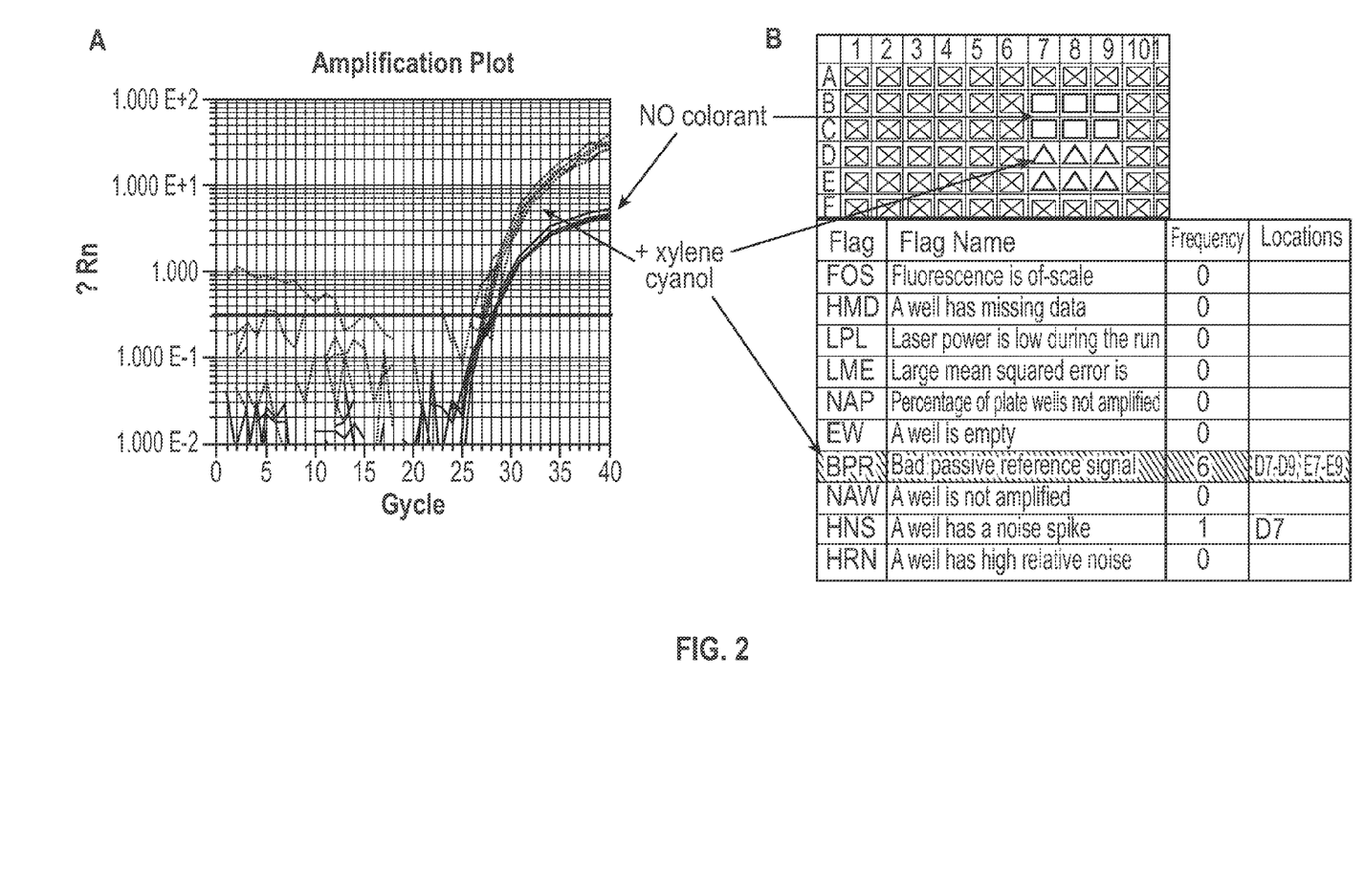
FIG. 2. Visible colorant, Xylene Cyanol, interferes ROX normalization and a composite colorant prevented the interference on 7900HT instrument. PCR amplification curves using a qPCR master mix with "no colorant" control (A, "no colorant") and that with a "xylene cyanol" blue colorant (A. "+xylne cyanol"). The added blue dye interfered and reduced ROX signal significantly (D, arrow) from the control (C. arrow), resulting in bad passive reference signal (BPR) QC flags (B, "+xylene cyanol"), and noisy amplification traces and larger Cq standard deviations (A, "+xylene cyanol"). LSD in a composite blue colorant compensated the loss of ROX signal (E, arrow) that prevented bad passive reference signal from happening.

FIG. 2A-2B show data from amplification of the above samples on a AB 7900 instrument. The reactions with the visible dye colorant had a lower ROX signal and an earlier Cq and higher end relative fluorescence units (RFU) than the reactions of no colorant control, indicating that the presence of the visually-detectable dye interfered with signal from ROX.

FIGS. 2C, D, and E are multicomponent data from the AB7900 instrument illustrating the ROX signal difference between different reactions, with the arrow indicating ROX signal (i.e., fluorescence signal at 620 nm). FIG. 2C shows the normal ROX signal in a reaction of no colorant control. FIG. 2D shows that inclusion of a visible dye Xylene Cyanol FF reduces ROX signal to a lower level from the no colorant control in 2 C. FIG. 2E shows that addition of a composite colorant that comprises a visible dye Xylene Cyanol and a long Stokes shift dye (mF6620C) compensates for the interference by the visible dye alone, resulting in increased ROX signal to its normal level as in the 2 C. Similar results were observed when the experiment was repeated with a composite colorant comprising a visible dye Xylene Cyanol and a compensating amount of ROX on a ViiA7 instrument.

Example 2

A Sample Concentrated Composite Colorant Stock Solution

A 200× concentrated composite colorant stock solution is prepared that contains 0.65 mg/ml of Xylene Cyanol FF, 3 μM ROX, 20 μg/ml mFG620C, in TE buffer (10 mM Tris, 0.1 mM EDTA, pH8) containing 0.02% Tween-20. The 200× colorant stock solution can be stored for long term at −20 C, or for short term at 4 C.

Example 3

Use of Composite Colorant for Tracking Pipetting of 2×PCR Mastermixes

The 200× composite colorant stock solution is used to convert a colorless qPCR or RT-qPCR master mix into a colored master mix by adding and mixing 10 μl of the 200× colorant into a 1 ml of colorless 2× master mix solution. This process only affects the 2× master mix concentration by less than 1% which can be ignored for general qPCR amplifications. The colored 2× master mix is then used as usual in qPCR reaction set-up, but with the advantage of being able to visually monitoring the pipetting and loading of the 2× master mix into a microwell PCR plate to avoid pipetting errors in reaction set-up. Since the composite colorant contains the ROX and mFG620C passive reference dyes at a concentration just enough to compensate for the visible dye Xylene Caynol FF interference and reduction of the internal passive reference dye in the mastermix when used on a real-time PCR instrument that requires passive reference signal for reporter signal normalization, this composite colorant can be used with any qPCR master mixes (e.g., those from Applied Biosystems that contain a FRET ROX as the passive reference dye, or those from Bio-Rad that contain both a simple ROX and a long Stokes shift passive reference dye mFG620C, intended for using on all different PCR instruments; or those from other venders that contain either a low concentration of ROX for the 7500 or ViiA 7 instruments, or a high concentration of ROX for 7900 and StepOne series instruments).

Example 4

Use of Composite Colorant for Tracking Pipetting of Samples

The 200× composite colorant stock solution is used with other component solutions for monitoring their pipetting/loading accuracies in PCR reaction set-up. The composite colorant stock solution is diluted to an appropriate concentration (e.g. 4×) into DNA sample solutions to make them visually traceable. 2.5 µl of colored DNA samples is pipetted into microplate wells that have been loaded with 7.5 µl qPCR assay mix (containing 5 µl of 2× qPCR master mix, 1 µl of 10× assay primer/probe mix, and 1.5 µl water).

Example 5

Use of Composite Colorant for Tracking Pipetting of Reaction Mix for qPCR Assay Panel Plates The 200× composite colorant stock solution is used for monitoring pipetting of reaction mix onto qPCR assays panel plate where different qPCR assays (assay primer pair mixes or assay primers and probe mixes) have been pre-dispensed and dried onto different wells in a microwell PCR plate. In this case, the 200× composite colorant stock solution is diluted into 1× concentration in a single PCR reaction mix that contains every components needed for qPCR except the assays primers/probes. This colored primer/probe-free reaction mix is then pipetted into the microwells of the qPCR assays panel plate, with good visually-traceable blue color for monitoring pipetting progress and accuracies.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composite colorant formulation comprising:
   a visually-detectable dye; and
   an internal reference molecule comprising a first fluorophore, which first fluorophore upon excitation emits energy at a specific wavelength range;
   wherein:
   the visually-detectable dye partially absorbs energy at the specific wavelength range; and
   the formulation does not comprise sufficient components for target nucleic acid amplification if added to a target nucleic acid and primers.

2. The composite colorant formulation of claim 1, wherein the specific wavelength range is peaked at between 615 and 625 nm.

3. The composite colorant formulation of claim 1, wherein the first fluorophore is a 5-and/or 6-carboxy-X-rhodamine dye.

4. The composite colorant formulation of claim 3, wherein the concentration of the 5-and/or 6-carboxy-X-rhodamine dye is more than 100 nM.

5. The composite colorant formulation of claim 1, wherein the internal reference molecule comprises a second fluorophore and a linker joining the first and second fluorophores such that excitation of the second fluorophore results in transfer of energy from the second fluorophore to the first fluorophore, which first fluorophore in turn emits energy at the specific wavelength.

6. The composite colorant formulation of claim 5, wherein the second fluorophore is fluorescein amidite (FAM).

7. The composite colorant formulation of claim 1, wherein the visually-detectable dye is selected from the group consisting of Xylene Cyanol FF, Cresol Red, Tertrazine, Quinoline Yellow, m-Cresol Purple, Brilliant Blue, Patent Blue, Indigocarmine, Acid Red 1, Neutral Red, Bromocresol Green, Acid Violet 5, Bromo phenol blue, and Orange G.

8. The composite colorant formulation of claim 1, wherein
   the visually-detectable dye is at an integer multiple of a visually-detectable concentration; and
   the internal reference molecule is at said integer multiple of a sufficient concentration to compensate for absorbance of a passive reference signal in a qPCR reaction by the visually-detectable dye at the specific wavelength range;
   wherein said integer multiple is between 2 and 1000.

9. The composite colorant formulation of claim 1, further comprising a long Stokes-shift passive reference dye different from the internal reference molecule, wherein the long Stokes-shift dye has a Stokes-shift greater than the Stokes-shift of the first fluorophore, wherein the long Stokes-shift dye has an emission wavelength maximum approximately the same as the first fluorophore emission wavelength maximum, and an excitation wavelength maximum at least 60 nm different than the first fluorophore excitation wavelength maximum.

10. The composite colorant formulation of claim 9, wherein the long Stokes-shift dye has a Stokes-shift of at least about 60 nm.

11. The composite colorant formulation of claim 9, wherein the long Stokes-shift dye has a excitation wavelength maximum of 550 nm or less.

12. The composite colorant formulation of claim 9, wherein said long Stokes-shift dye is a fluorescent dot.

13. The composite colorant formulation of claim 1, wherein the internal reference molecule is a long Stokes-shift dye, wherein the long Stokes-shift dye has an emission wavelength maximum approximately the same as a 5-and/or 6-carboxy-X-rhodamine dye emission wavelength maximum, and an excitation wavelength maximum of about 550 nm or less.

14. The composite colorant formulation of claim 1, wherein the formulation lacks a polymerase, nucleotides, or divalent cations.

15. A method of forming a mixture capable of supporting nucleic acid amplification, the method comprising,
   combining the composite colorant formulation of claim 1 with at least a DNA polymerase, nucleotides, divalent cations, a passive reference dye for amplification normalization and a nucleic acid sample, to form a mixture, wherein when said mixture is submitted to thermocyclic amplification conditions results in an amplification product.

16. The method of claim 15, comprising combining the composite colorant formulation with a real-time PCR master mixture comprising at least a DNA polymerase, nucleotides, divalent cations, a passive reference dye for amplification normalization, thereby forming a colored real-time PCR master mixture; and
   combining a nucleic acid sample with the colored real-time PCR master mixture.

17. A method of performing a real-time quantitative polymerase chain reaction, the method comprising,
performing a polymerase chain reaction (PCR) with a mixture comprising the composite colorant formulation of claim 1 and at least a DNA polymerase, nucleotides, divalent cations, a passive reference dye for amplification normalization, and a nucleic acid sample.

* * * * *